United States Patent [19]

Chowdhury

[11] 4,020,682

[45] May 3, 1977

[54] METHOD OF MEASURING MECHANICAL DAMAGE TO GRAIN

[75] Inventor: Mofazzal Hossain Chowdhury, Ames, Iowa

[73] Assignee: Iowa State University Research Foundation, Inc., Ames, Iowa

[22] Filed: June 16, 1976

[21] Appl. No.: 696,736

[52] U.S. Cl. ............................. 73/104; 73/432 R
[51] Int. Cl.² ...................................... G01N 33/02
[58] Field of Search ....................... 73/104, 432 R

[56] References Cited

UNITED STATES PATENTS 2,525,789  10/1950  Frankenfeld .................. 73/432 R Primary Examiner—James J. Gill
Attorney, Agent, or Firm—Tilton, Fallon, Lungmus, Chestnut & Hill

[57] ABSTRACT

Mechanical damage to grain is measured by taking a small sample of the grain and applying a solution of a substance which will selectively adhere only to the exposed surface of the interior of the damaged grain and not to the seed coat. Excess solution is rinsed away; and thereafter a solvent which will dissolve the substance adhering to the exposed internal parts of the grain is applied. The amount of recovered material brought back into solution is then measured; and the measurement is representative of the mechanical damage to the grain.

13 Claims, 9 Drawing Figures

METHOD OF MEASURING MECHANICAL DAMAGE TO GRAIN

BACKGROUND AND SUMMARY

The present invention relates to a method of measuring damage to grain; and more particularly, it is directed to measuring the mechanical damage to grain kernels, such as corn, which occurs during harvesting, drying and handling. Although the disclosure deals specifically with corn, persons skilled in the art will readily appreciate that the method of the present invention may be applied to other grain kernels which are subject to mechanical damage during harvesting and subsequent handling operations.

Standing in the field, unhusked corn is undamaged and can last almost indefinitely in that state without diminishing its food value. Deterioration begins with the mechanical process of harvesting, and practically every subsequent operation in the drying, transporting and handling further decreases the quality of the grain. The rate of deterioration is dependent on the initial injury sustained during such mechanical processes, particularly the harvesting operation.

During harvesting, the kernels are subjected to damaging impact and compressive forces which result in breaches of the seed coat or cracks in the pericarp of the kernel. Mold may grow in the cracks or interstices of the corn kernels to such an extent that an entire shipment may be destroyed.

Currently, practically no measurements are made concerning mechanical damage of grain at the initial selling point, and no discounts are applied, therefore, for mechanical damage. Hence, there is little or no incentive for the producer of the crop to minimize mechanical damage. Rather, the incentive is to maximize the retrieval of kernels, irrespective of the final condition of the kernels. Further, there is no commercial apparatus or method available for measuring mechanical damage to corn as it is being harvested which is economical, reliable, and administered without skilled help. If such a method were available, farmers could adjust their combines to minimize the mechanical damage which would result in great savings and which could be passed on to consumers.

A number of indices or tests have been proposed for measuring mechanical damage, but these have been primarily of a theoretical or academic interest. It is believed that much of the waste due to mechanical damage could be reduced or eliminated if, for example, grain elevators or markets could establish a purchase price based, at least in part, on discounts for mechanical damage of the corn as it is delivered. This would add some incentive to the farmer who properly adjusts his combine to minimize mechanical damage.

Without a standard of measuring mechanical damage, the equipment manufacturer cannot determine when he has developed an improved harvesting machine, in the sense that it minimizes mechanical damage for a given recovery rate. Further, the farmer cannot determine when he is harvesting grain of better quality, and the grain industries cannot determine when they are processing a product of higher quality.

The U.S. Department of Agriculture has developed a numerical grading system, but is was established at a time when corn and other grains were shelled at a low moisture content, with minimal damage. Modern combines harvest a grain crop at high moisture content; and the mechanical processes used subject the kernels to substantial compressive forces which sometimes introduce substantial damage. For example, shelled corn from a combine may contain a small portion of grain fines. However, the bulk of the kernels may be seriously damaged, and the grading system mentioned above does not account for various degrees of mechanical damage.

Visual inspection has been used by research workers for accurate evaluation of mechanical damage; but this method is time-consuming and produces fatigue which influences the results.

Other tests, such as a standard germination test, an acid germination test, the tetrazolium test and a carbon dioxide production test, give good indications of mechanical damage, but take too much time to be applied, for example, at the point of purchase. Other techniques like the corn breakage tester, the electric color sorting technique and infrared photographic techniques do not give a true and accurate picture of the extent of the damage. One of the reasons for this is that some of these tests are dependent upon grain orientation or they do not respond to the depth of a breach. Other experimental methods, such as the water absorption method, the light absorption method, and a relaxation time method are not sensitive enough to distinguish the damage level between samples.

In the present invention, mechanical damage to grain is measured by taking a small sample of the grain and applying a solution of a substance which will selectively adhere only to the exposed surface of the interior of the damaged grain and not to the seed coat. Excess solution is rinsed away, and thereafter a solvent is applied which will dissolve the substance adhering to the exposed internal portion of the grain.

The amount of recovered material brought back into solution is then measured—for example, its absorbance may be measured by a spectrophotometer.

A preferred material for use in selectively adhering to the starchy area of inner portion of the grain is a dye. The mechanical damage in the sample may be represented as the total area of the kernels exposed through breach. The total amount of dye absorbed by the grain is representative of the total exposed area. Hence, the amount of dye recovered back into solution, and therefore, the concentration of the dye in the solution is representative of the mechanical grain damage. Hence, the absorbance of the solvent, as measured by a spectrophotometer or a colorimeter, is representative of the mechanical damage to the sample. The present invention thus provides a fast and efficient method for accurately determining the quality of grain. It is simple in application and does not require the use of skilled personnel. It provides statistically sound results so that it may be applied as a bulk method simply by using a sample of a large quantity of grain to be tested. The present method provides quantitative as well as qualitative results. Further, the present invention provides a damage measure which accounts for all of the various types of damage to grain, from hairline cracks and tiny spots of missing pericarp to complete breakage and fines. In other words, the entire range of damage is measured as a continuum, with the result being an overall measure of total damage.

Other features and advantages of the present invention will be apparent to persons skilled in the art from the following detailed description of a preferred embodiment accompanied by the attached drawing.

THE DRAWING

DETAILED DESCRIPTION

According to the present invention, a sample of grain to be tested for damaged kernels is taken. The size of the sample is not important, but obviously for comparison purposes and for statistically sound results, the size of the sample should be uniform from test to test. A damaged kernel is defined as one which has any rupture or breach in the seed coat, irrespective of the severity of the breach or the amount of interior that has been exposed.

The sample is treated with a chemical substance which will selectively adhere only to the exposed area of the damaged grain, and not to the seed coat. One such substance (although other will be discussed and still others will be apparent to persons skilled in the art) is a Fast Green FCF Dye. This dye adheres to the starchy interior portion of a corn kernel, but it does not adhere to the seed coat, although it does adhere slightly to the top of the kernel.

After the application of the dye, excess non-adhering dye is washed away. The next step is to apply a solvent which will dissolve the dye adhering to the exposed interior part of the grains. In one instance, sodium hydroxide was used to dissolve the dye adhering to the exposed interior portion of the kernels, thereby "bleaching" the kernel.

The substance which adheres to the exposed interior portion of the kernels should follow the Lambert-Beer law so that the amount of dye present in the sample can be directly measured by some colorimetric method, such as using a simple colorimeter or a spectrophotometer. A simple measurement may be made to determine whether a substance obeys the Lambert-Beer law. The test is to measure, with all other things remaining constant, the absorbance as a function of concentration of the substance. If absorbance is a substantially linear function of concentration, then the law is satisfied, and that substance may be used in the present invention, provided it selectively adheres to the exposed interior portions of the grain under test and can later be removed by appropriate treatment. Absorbance is defined as the fraction of incident light which does not reach the other side.

Next, the absorbance of the material recovered from the damaged grain is measured. As indicated, a simple colorimetric technique may be used, or, if it is available, a spectrophotometer may be used to measure the absorbance. The latter is more expensive, but it is also more accurate.

Figure 1:
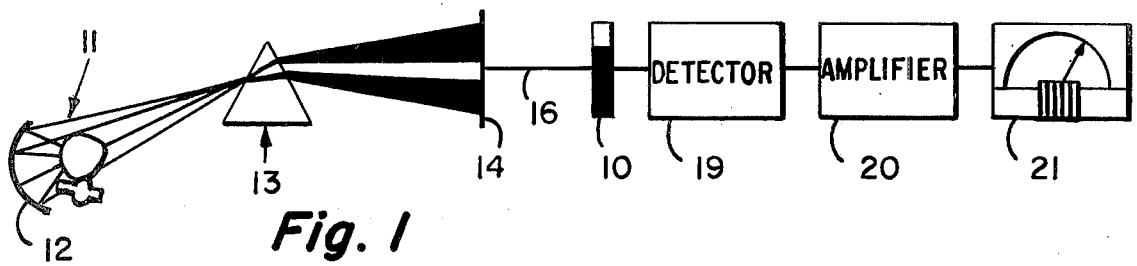
FIG. 1 is a schematic diagram of one method for measuring the right absorbance of a sample of a solution which has recovered that portion of the material that selectively adhered to the interior portion of the grain.

Although other measuring techniques may equally well be employed FIG. 1 illustrates one method that can be used for measuring the absorbance of the material recovered from the damaged grain. The sample being measured is held in a container 10. A source of light generally designated 11 transmits light to a parabolic mirror 12 which focuses the light onto a prism 13 which separates the incident light into its various spectral components. The resulting separated light is transmitted to a member 14 which includes a slit through which monochromatic light, indicated by the line 16 is passed. A detector, such as a photomultiplier tube, shown within the block 19 receives that portion of the light 16 which passes through the sample 10, and generates an electrical signal representative of the intensity of the sensed light. The electrical signal is fed to an amplifier 20 which drives a meter 21. The meter 21, therefore, generates a signal representative of the absorbance of the material in the container 10, provided, of course, that the system had been calibrated prior to the measurement.

THE DYE

The requirements of the dye are: (1) that is selectively adhere to the exposed interior portion of the damaged grain and not to the seed coat; (2) that it be recoverable after adhering to the exposed portion (e.g., it may either not chemically react with the interior portion of the grain, or if there is a reaction, it is reversible); and (3) that it substantially obey the Lambert-Beer law. There are a number of substances, particularly dyes (and associated solvents) that may be used. In one experimental aspect in connection with the present invention, Fast Green FCF dye [P, P'—Dibenzyl-diethyldiamino—P''—hydroxytriphenyl carbinol trisulfonic acid anhydride, disodium salt] and sodium hydroxide solution were used as the dye and solvent respectively for the evaluation of mechanical damage to grain, and corn was used as the grain.

The dye can be prepared to any desired concentration. To prepare 0.1 percent dye solution, 1 gram of Fast Green FCF dye was dissolved in 1,000 ml. of distilled water.

Figure 4:
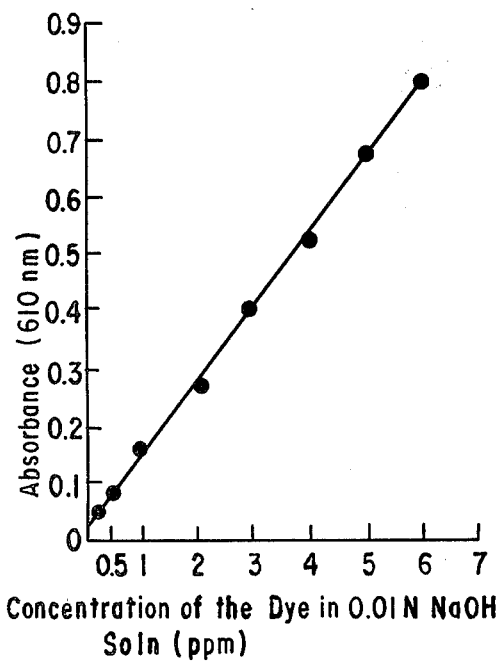
FIG. 4 is a graph showing the relationship between absorbance and concentration of the adhering agent.

In order to determine whether the dye follows the Lambert-Beer law, absorbance was measured as a function of concentration of the dye in the 0.01N NaOH solution. As seen in FIG. 4, the relationship is substantially linear, so the dye obeys the Lambert-Beer law.

Figure 7:
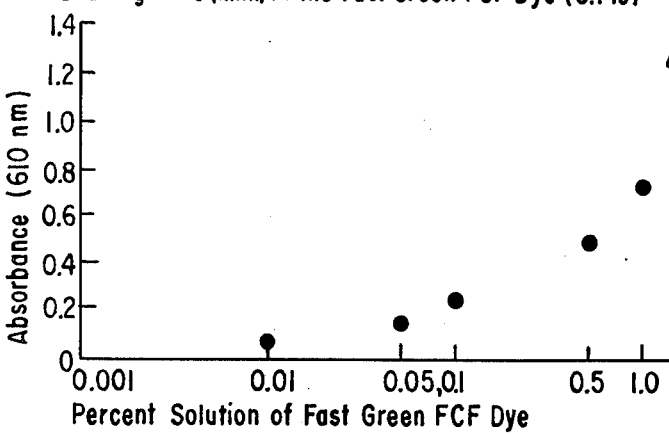
FIG. 7 is a graph showing the relationship between absorbance and the percent solution of the selective adhering agent.

The effect of the concentration of the dye (that is, the percent in solution) on absorbance is shown in the graph of FIG. 7. The concentration of the dye in the application solution should, of course, be maintained constant from test to test, but the concentration may be in the range of 0.001 percent through 1.0 percent for best results. Preferably, the concentration of the Fast Green FCF dye is 0.01 percent.

APPLICATION OF ADHERING MATERIAL

Figure 6:
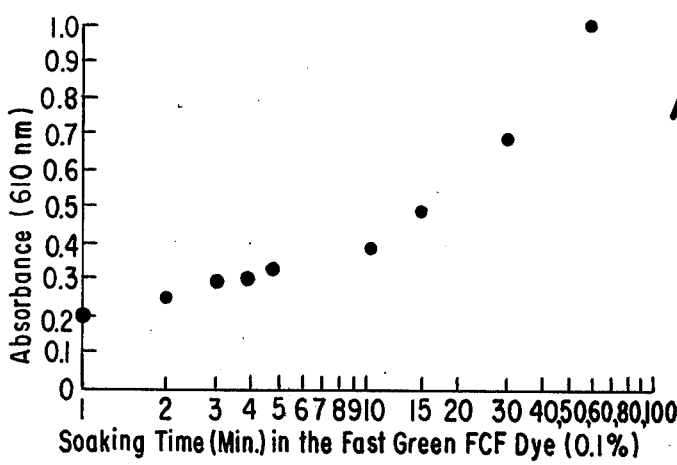
FIG. 6 is a graph showing the relationship between absorbance and soaking time of the sample in a solution containing the selective adhering agent.

The method of applying the dye to the sample of grain under test is simply to soak the sample in the solution containing the dye. Referring to FIG. 6, there is shown the effect of soaking time (on a logarithmic scale as the abscissa) with absorbance as the ordinate. These measurements were taken for different samples of known and constant damage, the preparation of which will be discussed below.

It will be observed from FIG. 6 that the absorbance may be increased with increased soaking time, but that reasonable results may be obtained from soaking times as little as 0.25 min. to 10 minutes. Soaking times of the order of ½–2 minutes will produce reasonable results, and have the advantage that the test may be performed on a continuous basis.

After the dye has been applied to the grain sample, the dye is poured off, and excess dye is removed from the seed coat by washing the sample under running water until clean water comes off the sample. Thirty seconds of such washing is normally adequate.

THE RECOVERY SOLVENT

The recovery solvent is a water solution of a base, such as sodium, potassium or ammonium hydroxides. Further, with Fast Green FCF dye as the adhering substance, in addition to these three bases, alcohol and acetone have successfully been used as the recovery solution.

Figure 8:
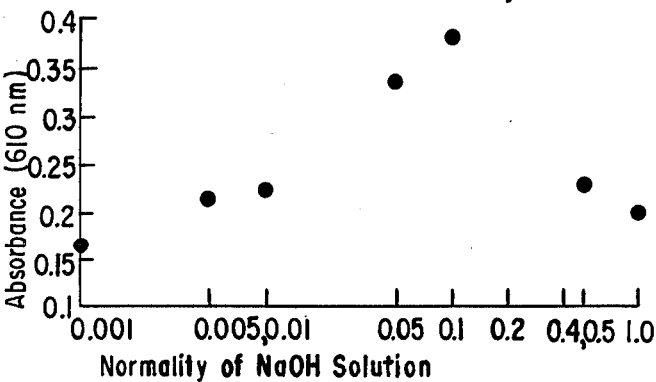
FIG. 8 is a graph showing the relationship between absorbance and the normality of the recovery solvent.

To prepare 1N of sodium hydroxide solution, 40 grams of NaOH are dissolved into 1,000 ml. of distilled water. To prepare 0.01N NaOH solution 10 ml. of 1N NaOH solution is added to 990 ml. of distilled water. The effect of the normality of the solvent on absorbance is shown graphically in FIG. 8. Briefly, the normality of the sodium hydroxide solution is not critical, although a normality of 0.01 is preferred.

Figure 5:
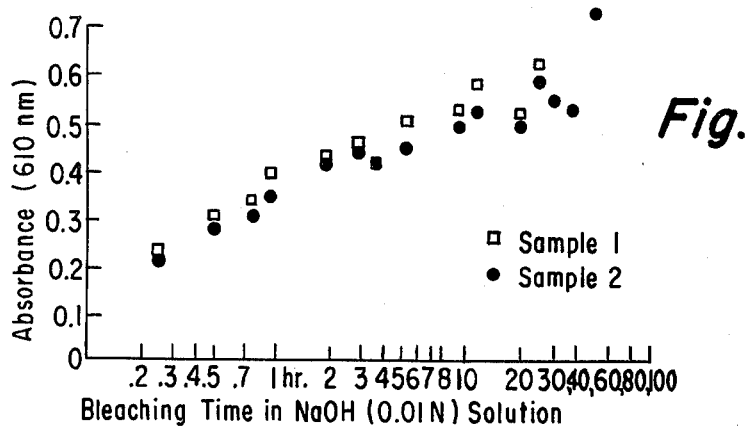
FIG. 5 is a graph showing the relationship between absorbance and the recovery or bleaching time.

Referring to FIG. 5, there is shown the relationship between the application time of the recovery solvent, or "bleaching" time, as it affects absorbance, for two different samples and for a number of bleaching times. Although the absorbance increases in a general linear fashion with increased bleaching time, nevertheless, good results may be obtained for short bleaching times, of the order of 0.5–15 minutes. Times of up to 1 hour have also been found satisfactory.

Figure 9:
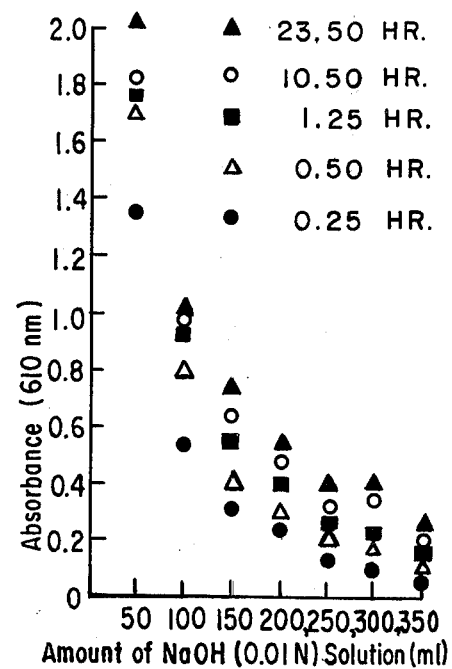
FIG. 9 is a graph showing the relationship between absorbance and the amount of recovery solvent for different bleaching times.

This time relation dye concentration in the solvent is further illustrated in the results depicted in FIG. 9 which shows the effect of the amount of bleaching solution (0.01N NaOH) used on absorbance, for five different application times ranging from 15 minutes to 23½ hours. For best results, absorbance should be in the range 0.1–0.8. Good measurements are obtained for larger amounts of bleaching solution.

As indicated, mechanical damage in actual harvesting and handling occurs on a continuous scale, ranging from hair-line cracks and tiny spots of missing pericarp to complete breakage; but it is difficult to control the level of damage for experimental purposes in order to determine the effect of various parameters. Hence, artificially damaged kernels were used as a control for this purpose. Mechanical damage can occur on any part of the kernel. For example, the tip, seed coat, embryo, endosperm, horny endosperm, crown, or any combination of these may be damaged. In the test results described thus far, artificially damaged corn kernels were prepared by cutting the kernel longitudinally so that all of the above-mentioned parts of the seed were exposed to the dye. Thus, the results illustrated in FIG. 5 were taken with two different artificially-prepared samples, and the closeness of results may be observed.

Figure 3:
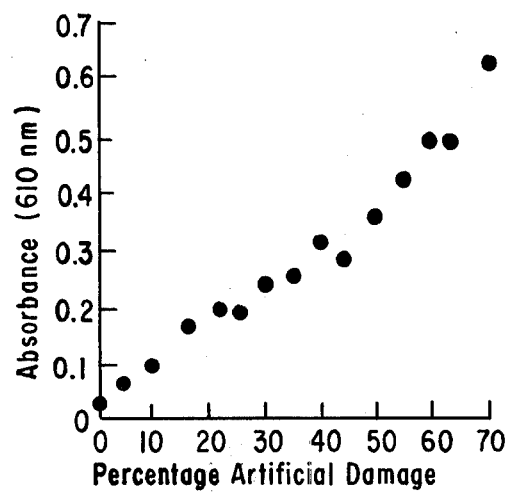
FIG. 3 shows the relationship between absorbance and percent damage for a control sample.

Referring now to FIG. 3, there is graphically illustrated the effect of the percentage of damage (that is, artificially-induced damage as just discussed) on absorbance. The relationship of an increasing absorbance with increasing percent damage can be seen. In all of the test results, a Beckman Instruments Model DB-G grating spectrophotometer having a cell thickness of 1 cm. and using a wavelength of 610 nm. was used to read the absorbance of the dye in the recovery solution. Distilled water was used as the reference solution in the reference cell because the recovery solution was an aqueous solution. The spectrophotometer was calibrated for zero absorbance with distilled water in both cells.

EXAMPLE I

Samples of corn were collected which were actually harvested by combines. The varieties of corn were unknown and the moisture content was known to be low. These samples had been visually inspected for damage evaluation and a damage level was established. A sample of 50 grams of corn was used, and it was soaked in 0.1 percent Fast Green FCF dye for 10 minutes. The sample was then washed under running water for 30 seconds to remove extra dye on the surface of the seed coat. The only places where the dye remained were on the exposed interior portions of the kernel and on the tip, as determined visually.

Figure 2:
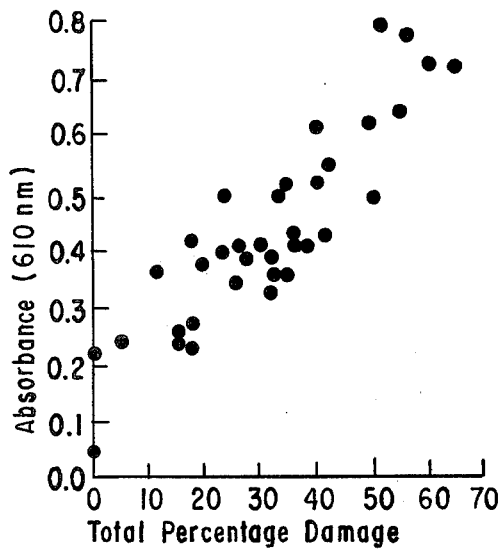
FIG. 2 is a graph showing the relationship between absorbance and percent damage for various damaged samples.

The sample was then re-soaked in 300 ml. of 0.01N NaOH solution. The sample was stirred for 1 minute and then allowed to settle for 15 minutes before measuring the absorbance of the recovery solution. The spectrophotometer identified above was used for measuring absorbance. The relation between the absorbance and the total percentage damage of the sample, as evaluated by visual inspection, is shown in FIG. 2. Although no statistical test was performed on the results, they did show a positive correlation between the total percentage damage and the measured absorbance, as can be seen from FIG. 2. Further, a correlation was observed between the measured absorbance and a damage figure which was developed for critical evaluation of grain damage and designed to take into account the entire range of damage encountered during modern harvesting and handling processes. This damage index is defined in our article entitled "Development of a Numerical Damage Index for Critical Evaluation of Mechanical Damage of Corn", presented at the American Society of Agricultural Engineers meeting in St. Joseph, Mo., on Mar. 21–22, 1975.

EXAMPLE II

Samples for this example were collected from a John Deere Model 95 stationary combine cylinder. Three levels of cylinder speed were used: 450, 500 and 600 rpm. respectively. Two levels of front concave clearance were used: ¾ in. and 1 3/16 in. The rear concave clearance were used: ¾ in. and 1 3/16 in. The rear concave clearance was kept constant at ⅝ in. Two replications were taken for each set of machine parameters. The corn used was of mixed variety. The kernel moisture content while shelling was 21 percent (w.b.) and was dried to 14 percent before damage evaluation.

A Boerner divider was used to obtain samples of 50 grams for damage evaluation, and these samples were prepared by the method indicated above except that they were soaked in 250 ml. of 0.01 N NaOH solution. The results are shown in Table I.

TABLE I

| Front concave clearance (in.) | Cylinder rpm | Replication | Total percent damage | Mean damage | Absorbance | Mean absorbance |
|---|---|---|---|---|---|---|
| 3/4 | 450 | 1 | 22.6 | | 0.320 | |
| | | | | 21.45 | | 0.32 |
| 3/4 | 450 | 2 | 20.3 | | 0.320 | |
| 3/4 | 500 | 1 | 29.3 | | 0.405 | |
| | | | | 33.65 | | 0.415 |
| 3/4 | 500 | 2 | 38.0 | | 0.425 | |
| 3/4 | 600 | 1 | 38.06 | | 0.565 | |
| | | | | 37.34 | | 0.582 |
| 3/4 | 600 | 2 | 36.62 | | 0.600 | |
| 1-3/16 | 450 | 1 | 23.2 | | 0.450 | |
| | | | | 22.97 | | 0.375 |
| 1-3/16 | 450 | 2 | 22.74 | | 0.300 | |
| 1-3/16 | 500 | 1 | 24.94 | | 0.295 | |
| | | | | 21.92 | | 0.307 |
| 1-3/16 | 500 | 2 | 18.90 | | 0.320 | |
| 1-3/16 | 600 | 1 | 29.1 | | 0.485 | |
| | | | | 25.85 | | 0.400 |
| 1-3/16 | 600 | 2 | 22.6 | | 0.315 | |

In each case, after an absorbance reading was taken, the recovery solution was drained from the samples and the samples were dried to their original weight for a visual damage analysis. The samples were visually inspected under a magnifying glass for damage evaluation. The mechanical damage has been defined in this case as the percent of total weight consisting of fines, chipped kernels, kernels with big or hairline cracks, and kernels with spots of pericarp missing. Again, the results are shown at the lower portion of Table I, and between these two sets of tests, it was observed that the relation between rpm. of the combine and the percentage total damage and absorbance did follow the same pattern.

Referring back to FIG. 5, the artificially damaged samples which were tested as explained above were prepared by adding split kernels (according to the percentage damage indicated in FIG. 3) with the sound hand-shelled kernels to make a 25-gram sample of each case. The samples were then completely soaked in 0.1 percent Fast Green FCF dye for 10 minutes and then washed under running water for 30 seconds. The samples were then re-soaked in 200 ml. of 0.01N NaOH solution for an hour. All the samples were stirred for 1 minute and were allowed to settle for 15 minutes before measuring absorbance. The results, as indicated, are graphically displayed in FIG. 5, and they did show a good correlation with expected variation.

OTHER MATERIALS

Using the above teachings, other systems of adhering and recovery materials have proved successful. For example methyl orange [4-NaOSO$_2$C$_6$H$_4$N; NC$_6$H$_4$1-4-N(CH$_3$)$_2$] is effective as the adhering material with recovery solutions of NaOH, KOH, NH$_4$OH and alcohol. The method was successful with methyl green (M-295, 735240 Fisher, certified biological stain) as the adhering material and alcohol as the recovery solution. Crystal violet [4-(CH$_3$)$_2$ NC$_6$H$_4$]$_2$C; C$_6$H$_4$ 4[:N(CH$_3$)$_2$Cl] worked with alcohol. Phenol red (phenolsulfonphthalein) worked with all these three bases; and blue red dye, as it is commonly known, worked with KOH, NH$_4$OH and alcohol as the recovery solution.

In summary, the present invention does provide a simple, economical and reliable test for quantitatively and qualitatively measuring mechanical damage of grain. The test may be performed within a few minutes (by selecting the proper concentration of dye and the right normality of the recovery solution). The method is accurate in describing the quality of grain from the standpoint of mechanical damage caused during harvesting, transportation and handling.

Having thus described in detail a preferred embodiment of the invention, persons skilled in the art will be able to modify certain of the steps which have been disclosed, and to substitute equivalent elements for those described, while continuing to practice the principle of the invention; and it is, therefore, intended that all such modifications and substitutions be covered as they are embraced within the spirit and scope of the appended claims.

I claim:

1. A method of measuring mechanical damage to grain comprising: applying to a sample of said grain a substance which will selectively adhere to the exposed surface of the interior of the damaged grain and not to the seed coat; applying a recovery solution to said sample which will remove said substance adhering to the exposed internal portions of the grain; and measuring the amount of said substance removed from said grain by said recovery solution, said measurement being quantitatively representative of the damage of said grain.

2. The method of claim 1 wherein said substance is an aqueous solution of a dye characterized in selectively adhering to the exposed surface of the interior portion of damaged grain and not to the seed coat, and in having an absorbance which is a substantially linear function of concentration.

3. The method of claim 2 wherein the absorbance of said substance is in the range 0.1 to 0.8.

4. The method of claim 1 wherein said adhering substance is a dye selected from the group consisting of Fast Green FCF, methyl orange, crystal violet, phenol red and blue red dye.

5. The method of claim 4 wherein said dye is Fast Green FCF dye having an absorbance in the range 0.1 to 0.8.

6. The method of claim 2 wherein said dye is applied to said damaged grain for a time in the range of 0.25 – 10 minutes.

7. The method of claim 6 wherein said dye comprises a 0.1 percent solution of Fast Green FCF dye.

8. The method of claim 1 further comprising the step of removing excess adhering solution from said sample prior to measuring by rinsing said sample in water.

9. The method of claim 1 wherein said removing solution is selected from the group of sodium hydroxide, potassium hydroxide and ammonium hydroxide.

10. The method of claim 9 wherein said hydroxide is supplied in aqueous solution to said sample for a time in the range of 0.5 minutes to one hour.

11. The method of claim 1 wherein said step of measuring comprises measuring the absorbance of said recovery solution.

12. The method of claim 11 wherein said step of measuring comprises measuring absorbance of said recovery solution at a single wavelength of light.

13. A method of measuring mechanical damage to grain comprising applying an aqueous solution of Fast Green FCF dye to a sample of grain for a time in the range of 0.5 – 10 minutes, the absorbance of said dye being in the range 0.1 – 0.8; removing said sample from said solution and rinsing excess dye from said sample with water; applying a a predetermined amount of a recovery solution selected from the group consisting of NaOH, KOH and NH$_4$OH to said sample for a time in the range of 0.5 minutes to 1 hour to remove dye adhered to the exposed interior portions of said sample; and then measuring the absorbance of said solvent solution.

* * * * *

UNITED STATES PATENT AND TRADEMARK OFFICE
CERTIFICATE OF CORRECTION

PATENT NO. : 4,020,682
DATED : May 3, 1977
INVENTOR(S) : Mofazzal Hossain Chowdhury It is certified that error appears in the above–identified patent and that said Letters Patent are hereby corrected as shown below:

In claim 1, column 8, line 49, change "of" second occurrence, should read -- to --.

Signed and Sealed this twenty-sixth Day of July 1977

[SEAL]

Attest:

RUTH C. MASON
*Attesting Officer*

C. MARSHALL DANN
*Commissioner of Patents and Trademarks*